United States Patent [19]

Zarchy et al.

[11] Patent Number: 5,705,730
[45] Date of Patent: Jan. 6, 1998

[54] ISOMERIZATION PROCESS WITH IMPROVED CHLORIDE RECOVERY

[75] Inventors: Andrew S. Zarchy, Kildeer, Ill.; Lawrence Tucker Kass, White Plains, N.Y.

[73] Assignee: UOP, Des Plaines, Ill.

[21] Appl. No.: 753,072

[22] Filed: Nov. 20, 1996

[51] Int. Cl.$^6$ .................. C07C 5/13; C07C 7/12
[52] U.S. Cl. .......... 585/738; 585/737; 585/739; 585/741; 585/743; 585/742; 585/747; 585/748; 585/823; 585/820
[58] Field of Search .................. 585/737, 738, 585/739, 741, 743, 748, 823, 826, 742, 747

[56] References Cited

U.S. PATENT DOCUMENTS

| | | |
|---|---|---|
| 4,935,580 | 6/1990 | Chao et al. .................. 585/820 |
| 4,964,889 | 10/1990 | Chao .................. 55/58 |
| 5,164,076 | 11/1992 | Zarchy et al. .................. 208/245 |
| 5,336,834 | 8/1994 | Zarchy et al. .................. 585/737 |
| 5,516,963 | 5/1996 | Zarchy et al. .................. 585/737 |

Primary Examiner—Glenn Caldarola
Assistant Examiner—Thuan D. Dang
Attorney, Agent, or Firm—Thomas K. McBride; John G. Tolomei

[57] ABSTRACT

A process for the isomerization of hydrocarbons using a chloride promoted catalyst wherein an adsorption zone arrangement operates to maintain chloride compounds in the reaction zone and to prevent contamination of product streams with chloride compounds removes normal paraffins from the desorbent stream to extend the capacity and life of a clinoptilolite molecular sieve. The invention preferably uses isoparaffins recovered from the isomerization zone as a desorbent. A gaseous fraction of the isomerization zone effluent can be recovered to provide a desorbent containing a low concentration of normal paraffins.

20 Claims, 3 Drawing Sheets

□ 50% vol% Normal Hydrocarbons
▷ Non-Normal Hydrocarbons
◇ 25% vol% Normal Hydrocarbons

ISOMERIZATION PROCESS WITH IMPROVED CHLORIDE RECOVERY

BACKGROUND OF THE INVENTION

1. Field of the Invention

This invention relates generally to the catalytic conversion of hydrocarbons and the recovery of chloride compounds.

2. Description of the Prior Art

Many isomerization processes employ a highly effective chlorided platinum alumina catalyst system in the reaction zone. The chlorided catalyst requires a continual addition of chloride to replace chloride lost from the surface of the catalyst into the product stream. Hydrogen chloride and/or volatile organic chlorides escape from the process with a stabilizer overhead stream and, apart from the loss of chloride, pose environmental concern. In addition to the loss of chlorides and environmental concerns, chloride loss hinders the operation of chloride promoted isomerization zones in other ways. For example, the recycle of hydrogen or hydrocarbons by a zeolitic adsorption process is not practical when a chloride type catalyst is used unless hydrogen chloride is removed from the recycle stream. Hydrogen chloride produced by the addition of chloride to the reaction zone or released from the catalyst composite results in significant amounts of hydrogen chloride leaving the effluent from the isomerization zone. Contact of this hydrogen chloride with the crystalline alumino-silicates in adsorption or conversion zones will decompose the matrix structure of many crystalline alumino-silicates thereby destroying any catalytic or adsorptive function. Therefore, absent chloride neutralization methods, chlorided catalyst systems generally have insufficient compatibility with many zeolitic catalysts or adsorbents to permit simultaneous use.

U.S. Pat. No. 5,336,834 issued Zarchy et. al. discloses a chloride activated isomerization process that uses a thermal swing adsorption zone to recover hydrogen chloride from the isomerization zone and recycle the hydrogen chloride to the inlet of the isomerization zone. The process uses an acid tolerant molecular sieve to adsorb HCl from the stabilizer overhead and produce an HCl free effluent stream. The HCl is desorbed into the isomerization zone feed to completely contain the chloride compounds within the isomerization zone. Zarchy et. al teach the use of hydrocarbon feed as the desorbent to the isomerization zone. This feed is rich in normal hydrocarbons. It has been found that repeated adsorption and desorption of chloride compounds with isomerization zone effluent and feed streams diminish the chloride retention capacity of the acid resistant adsorbent.

It is an object of this invention to improve the methods of recovering and recycling chloride compounds in an isomerization process that uses a chloride promoted isomerization catalyst.

SUMMARY OF THE INVENTION

It is now been discovered that the life of an acid resistant adsorbent can be extended indefinitely by using a desorbent that is substantially free of normal hydrocarbons. In particular, it has been discovered that the desorbent should be substantially free of normal hydrocarbons containing more than three carbon atoms. The effect of the normal hydrocarbons and, in particular, the heavier hydrocarbons is to cause a progressive and permanent deactivation of the adsorbent. Therefore, by the elimination of normal hydrocarbons from the desorbent stream, this invention can provide an indefinitely longer life to an acid resistant adsorbent.

2

The benefits of this invention are further realized by the use of a specialized flow scheme for integrating the adsorption step with the isomerization process while essentially eliminating the passage of normal hydrocarbons as desorbent to an adsorbent containing adsorbed chloride compounds. For example, in a butane isomerization process, the flow scheme uses a deisobutanizer overhead product as a desorbent. The deisobutanizer overhead is substantially free of normal hydrocarbons. The selection of the deisobutanizer overhead stream permits desorption of the chloride-containing adsorbers with a substantially normal hydrocarbon-free stream. The flow scheme can also be arranged to prevent contacting of the adsorbent during the adsorption stage with heavy paraffins.

Accordingly in one embodiment this invention is a process for the isomerization of a hydrocarbon feed containing normal hydrocarbons with a chloride promoted catalyst. The process combines a feed stream comprising normal paraffins with a first desorption stream comprising a chloride compound and containing less than 10 wt % normal paraffins to produce a combined feedstream. The combined feedstream contacts a chloride promoted isomerization catalyst at isomerization conditions to convert normal paraffins to isoparaffins and produce an effluent stream comprising normal paraffins, isoparaffins and a chloride compound. At least a portion of the effluent stream passes to an adsorption zone that contacts the portion of the effluent with an adsorbent to adsorb chloride compounds from the effluent stream. A second desorbent stream containing less than 10 wt % normal paraffins enters the adsorption zone to desorb chloride compounds from the adsorbent and produce the first desorption stream. Isoparaffins from the effluent stream are recovered from the process.

In another embodiment this invention is a process for the isomerization of a hydrocarbon feed containing normal hydrocarbons with a chloride promoted catalyst that combines a feed stream comprising normal paraffins with a desorption stream comprising isoparaffins and a desorbed chloride compound to produce a combined feedstream. The combined feedstream contacts a chloride promoted isomerization catalyst at isomerization conditions to convert normal paraffins to isoparaffins and produce an effluent stream comprising normal paraffins, isoparaffins and a chloride compound. The effluent stream is passed to a first separator for recovery of an overhead stream containing the chloride compound and a bottoms stream comprising normal paraffins and isoparaffins. The overhead stream passes to an adsorption zone that contacts the overhead stream with a clinoptilolite molecular sieve to adsorb said chloride compound from the overhead stream. The bottoms stream passes to a second separator to separate normal paraffins from isoparaffins. An isoparaffin stream rich in isoparaffins is recovered from the separator. A portion of the isoparaffin stream passes to the adsorption zone to desorb chloride compounds from the desorbent and produce the desorption stream comprising isoparaffins and chloride compounds. A portion of the isoparaffin stream is recovered from the process as product.

Additional embodiments and details of this invention are disclosed in the following Detailed Description of the Invention.

DETAILED DESCRIPTION OF THE PREFERRED EMBODIMENTS

The preferred embodiment of this invention is in the isomerization of $C_4$–$C_6$ hydrocarbons. The products of isomerization processes contribute to a gasoline blending pool. Such gasoline blending pools normally include $C_4$ and heavier hydrocarbons having boiling points of less than 205° C. (395° F.) at atmospheric pressure. This range of hydrocarbons includes $C_4$–$C_7$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement is now often obtained by using isomerization to rearrange the structure of the straight-chain paraffinic hydrocarbons into branch-chained paraffins.

Preferred feedstocks for isomerization are rich in normal paraffins having from 4 to 6 carbon atoms or a mixture of such normal paraffins. The term "rich" is defined to mean a stream having more than 50% of the mentioned component. Other useful feedstocks include light natural gasoline, light straight run naphtha, gas oil condensate, light raffinates, light reformate, light hydrocarbons and straight run distillates having distillation end points of about 77° C. (170° F.) and containing substantial quantities of $C_4$–$C_6$ paraffins. The feed stream may also contain low concentrations of unsaturated hydrocarbons and hydrocarbons having more than 7 carbon atoms. The concentration of these materials should be limited to 10 wt. % for unsaturated compounds and 20 wt. % for heavier hydrocarbons in order to restrict hydrogen consumption and cracking reactions.

The isomerization of paraffins is generally considered a reversible first order reaction. The reaction is limited by thermodynamic equilibrium. The most common types of catalyst systems that are used in effecting the reaction are hydrochloric acid promoted aluminum chloride systems and supported aluminum chloride catalysts. The isomerization reaction zone typically contains a fixed bed of a chloride promoted isomerization catalyst. In the expectation that the feedstock will contain some olefins and, therefore, will undergo at least some cracking, the catalyst is preferably combined with an additional catalyst component that will provide a hydrogenation-dehydrogenation function. Preferably, this component is a noble metal of Group VIII of the periodic classification of the elements which are defined to include ruthenium, rhodium, platinum, osmium, iridium and palladium, with these specific metals being also known as the platinum group metals. The catalyst composition can be used alone or can be combined with a porous inorganic oxide diluent as a binder material. Other suitable binders include alumino-silicate clays such as kaolin, attapulgite, sepiolite, polygorskite, bentonite and montmorillonite, when rendered in a pliant plastic-like condition by intimate admixture with water, particularly when the clays have not been acid washed to remove substantial quantities of alumina.

Of these chlorided catalyst systems a particularly preferred type of catalyst consists of a high chloride catalyst on an alumina base containing platinum. The alumina may be selected from various forms including an anhydrous gamma-alumina with a high degree of purity. The catalyst may also contain other platinum group metals. These metals demonstrate differences in activity and selectivity such that platinum is the preferred metal for use in such catalysts. The catalyst will contain from about 0.1–0.25 wt. % platinum. Other platinum group metals may be present in a concentration of from 0.1–0.25 wt. %. The platinum component may exist within the final catalytic composite as an oxide or halide or as an elemental metal. The presence of the platinum component in its reduced state has been found most suitable for this purpose. The catalyst also contains the chloride component. The chloride component termed in the art "a combined chloride" is present in an amount from about 2 to about 10 wt. % based upon the dry support material. The use of chloride in amounts greater than 5 wt. % have been found to be the most beneficial in these catalysts.

There are a variety of ways for preparing a chlorided catalytic composite and incorporating a platinum metal and chloride therein. The method that has shown the best results impregnates the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-alumina catalyst base. An alternate method of increasing the chloride concentration in the final catalyst composite is to use an aluminum hydrosol to form the alumina carrier material such that the carrier material also contains at least a portion of the chloride. Chloride may also be added to the carrier material by contacting the calcined carrier material with an aqueous solution of the chloride such as hydrogen chloride.

When a chlorided catalyst is used, operation of the isomerization zones often uses a small amount of a chloride promoter. The chloride promoter, typically an organic chloride, serves to maintain a high level of active chloride on the catalyst as low levels are continuously stripped off the catalyst by the hydrocarbon feed. The concentration of promoter in the reaction zone is maintained at from 30–300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

These chloride promoted catalysts are very reactive and can generate undesirable side reactions such as disproportionation and cracking. These side reactions not only decrease the product yield but can form olefinic fragments that polymerize or deposit on the catalyst and shorten its life. One commonly practiced method of controlling these undesired reactions has been to carry out the reaction in the presence of hydrogen.

In accordance with this invention, an adsorption zone recovers the chloride that the feed strips from the catalyst. At least a portion of the effluent from the reaction zone contacts an adsorbent having a capacity for chloride compounds.

Unless otherwise noted the term "portion" in this specification when describing a process stream refers to either an aliquot portion of the stream or a dissimilar fraction of the stream having a different composition than the total stream from which it was derived.

The principle of the instant invention can be implemented with many different adsorbents such as zeolites, clays, inorganic polymers, alumina, silica gel, zirconia, carbon, organic polymers such as resin adsorbent, etc. Suitable adsorbents will have a selectivity and capacity for removal of chloride compounds in relatively low concentrations. Suitable adsorbents must also have an acid resistance to provide prolonged service in the chloride environment. Typically the chloride compounds will have a concentration of less than 3000 ppm in the effluent or effluent fractions from which the chloride compounds are adsorbed. The relatively small concentration of the chloride compounds in the isomerization effluent stream allow the process to use adsorbents have very low cyclic loadings. The process of this invention is viable with adsorbents that have cyclic loadings as low as 0.5 wt %. Preferably, the adsorbent material will recover 90 wt. % and, more preferably, more than 99 wt. % of the chloride compounds from the effluent or effluent fraction that it contacts.

Adsorbents that are known to benefit the most when used in this invention are ion-exchanged clinoptilolites particularly, NaK clinoptilolite, acid washed Ba clinoptilolite, acid washed Na clinoptilolite, MgK clinoptilolite, acid leached clinoptilolite, $NH_4$ clinoptilolite, etc. These adsorbents are particularly suitable for recovering and recycling HCl. Clinoptilolite as an adsorbent with adjustable pore size and acid resistance is described in U.S. Pat. No. 4,935,580 issued to Chao et al., U.S. Patent No. 4,964,889 issued to Chao, and U.S. Pat. No. 5,164,076 issued to Zarchy, Chao and Correia, the contents of which are hereby incorporated by reference. For NaK and MgK clinoptilolite, the preferred concentration of potassium ions is in the range of 15 to 75%, and more preferably in a range of 30 to 70%, and the concentration of Na and Mg are preferably in a range of 25 to 85% and more preferably in a range of 30 to 70%. The sum of Na and K or Mg and K are in the range of 50 to 100% of the total ion exchange capacity of the adsorbent. For Ba clinoptilolite, the barium concentration should be in the range of 20 to 100% of the ion exchange capacity. Other useful compositions include K, Na, Li, H, Mg, Ca, Sr, Zn, Mn, Co, CaK, SrK, ZnK, MnK, CoK and BaK cation exchanged or naturally occurring clinoptilolites and their acid washed version with the intended cations accounting for 50 to 100% of the total ion-exchange capacity of the clinoptilolite.

The most important factor in obtaining suitable clinoptilolite materials for the adsorption of HCl compounds is the adjustment of the adsorbent pore size. In most cases, the changes in the pore size of zeolites following ion-exchange are consistent with a physical blocking of the pore opening by the cation introduced. In general, in any given zeolite, the larger the radius of the ion introduced, the smaller the effective pore diameter of the treated zeolite (for example, the pore diameter of potassium A zeolite is smaller than that of sodium A zeolite), as measured by the size of the molecules which can be adsorbed into the zeolite.

Such is not the case, however, with clinoptilolites which demonstrate an unpredictable relationship that is not a simple function of the ionic radius of the cations introduced, i.e., pore blocking. For example potassium cations, which are larger than sodium cations, provide a clinoptilolite having a larger effective pore diameter than sodium ion-exchanged clinoptilolite. Sodium has an ionic radius of 0.98 Å versus 1.33 Å for potassium. See F. A. Cotton, G. Wilkinson, *Advanced Inorganic Chemistry*, Interscience Publishers (1980) or the *Handbook of Chemistry and Physics*, 56 Edition, CRC Press (1975) at pg. F-209, said references hereby incorporated by reference. In fact, a sodium ion-exchanged clinoptilolite with a sodium content equivalent to about 90% of its ion-exchange capacity defined by its aluminum content essentially excludes both hydrogen sulfide and n-butane. On the other hand, a potassium ion-exchanged clinoptilolite with a potassium content equivalent to about 95% of its ion-exchange capacity adsorbs hydrogen sulfide rapidly but substantially excludes n-butane. Thus, the clinoptilolite containing the cation with the larger ionic radius, i.e., potassium, has a larger pore than the clinoptilolite containing the cation with the smaller ionic radius, i.e., sodium.

The clinoptilolites used in the process of the present invention may be natural or synthetic clinoptilolites. Natural clinoptilolites are preferred because they are currently readily available in commercial quantities. However, natural clinoptilolites are variable in composition and chemical analysis shows that the cations in clinoptilolite samples from various mines and even within a single deposit can vary widely. Moreover, natural clinoptilolites frequently contain substantial mounts of impurities, especially soluble silicates, which may alter the adsorption properties during activation, or may cause undesirable side effects which may inhibit practicing this invention. As an example of the compositional variations in natural clinoptilolites, the following Table 1 sets forth the chemical analysis of several clinoptilolite ore samples.

TABLE 1

| Ore No. | 1 | 2 | 3 | 4 | 5 |
|---|---|---|---|---|---|
| Source No. | 1 | 2 | 3 | 2 | 1 |
| | Wt. % dry basis | | | | |
| $SiO_2$ | 76.37 | 76.02 | 75.24 | 76.67 | 76.15 |
| $Al_2O_3$ | 12.74 | 13.22 | 12.62 | 13.95 | 12.90 |
| MgO | 0.55 | 0.77 | 2.12 | 0.76 | 0.33 |
| CaO | 0.55 | 2.19 | 2.72 | 2.27 | 1.04 |
| $Na_2O$ | 3.86 | 3.72 | 2.25 | 3.26 | 4.09 |
| $K_2O$ | 4.21 | 2.11 | 2.17 | 1.93 | 4.08 |
| Other* | 1.72 | 1.98 | 2.88 | 1.16 | 1.41 |
| | 100.00 | 100.00 | 100.00 | 100.00 | 100.00 |
| | | Elemental Concentration mmol/gm | | | |
| Si | 12.73 | 12.67 | 12.54 | 12.78 | 12.69 |
| Al | 2.50 | 2.59 | 2.47 | 2.74 | 2.53 |
| Mg | 0.14 | 0.19 | 0.53 | 0.19 | 0.08 |
| Ca | 0.10 | 0.39 | 0.49 | 0.41 | 0.19 |
| Na | 1.25 | 1.20 | 0.73 | 1.05 | 1.32 |
| K | 0.89 | 0.45 | 0.46 | 0.41 | 0.87 |

*Includes the following oxides: $Fe_2O_3$, SrO, BaO

It can be seen from Table 1 that the concentrations of the various cations of the ore samples can vary quite substantially, especially when considered in view of the total theoretical ion-exchange capacity based on aluminum content. Note, for instance, the calcium content which varies from about 8 equivalent percent in Ore No. 1 to about 40 equivalent percent in Ore No. 3, e.g., for Ore No. 1, using the cation concentrations, Ca×2/Al×100=%, 0.10×2/2.5×100=8.0%. Similarly, the potassium content varies from 15.0 equivalent percent in Ore No. 4 to 35.6 equivalent percent in Ore No. 1. With respect to cations present in relatively small amounts such as barium or strontium, the variations are generally not significant.

Often, due to the above-described compositional variations, it is desirable to treat the natural clinoptilolite with a thorough ion-exchange to create a uniform starting material. For this initial ion-exchange, it is important to use a cation of reasonably high ion-exchange selectivity so it can effectively displace a substantial portion of the variety of cations originally existing in the natural zeolite. However, it is also important to not use a cation of overly high selectivity, otherwise it would make further tailoring of the adsorption properties of the clinoptilolite by ion-exchange difficult. The cations suitable to provide compositional uniformity in accordance with the present invention include sodium, potassium, calcium, lithium, magnesium, strontium, zinc, copper, cobalt, and manganese. It is often economically advantageous, and preferred, to use sodium or potassium for this purpose. The ion-exchanged clinoptilolite can then be further ion-exchanged with other cations, e.g., barium cations, to establish the desired level. It is, of course, possible to ion-exchange the clinoptilolite directly with cations other than those set forth above, e.g., barium cations, without an initial ion-exchange.

Clinoptilolite typically loses some of its adsorption capacity for HCl after adsorbing and desorbing HCl. However, the rate of loss slows drastically after the first few cycles. It has been found that NaK clinoptilolite, acid washed Ba clinoptilolite, acid washed Na clinoptilolite, MgK clinoptilolite, acid leached clinoptilolite (or H clinoptilolite) and acid washed $NH_4$ clinoptilolite all retain a substantial amount of HCl capacities after repeated adsorption and desorption in the absence of normal hydrocarbon desorbents. Another reason for the loss of HCl capacity after repeated cycles is the reaction of clinoptilolite cations with HCl to form chloride salt. In some cases, HCl washing to remove such chloride salt in the adsorbent manufacturing stage is helpful in providing a product that minimizes the phenomena of chloride salt formation and has a higher steady state HCl capacity.

The type and concentration of hydrocarbons present in the feedstream have been found to have an important impact on the performance of the adsorbent. Hydrocarbons for the isomerization process will generally be present in a carbon range of from about 1 to about 8 carbon atoms per molecule. Propane and lighter hydrocarbons are often by-products produced by cracking in the isomerization zone. The adsorbent should have a low capacity for these small hydrocarbon impurities. NaK clinoptilolite, acid washed Ba clinoptilolite, and MgK clinoptilolite, as previously described, have suitably low capacity for $C_3$ and lighter hydrocarbons and are preferred adsorbents.

In accordance with this invention the loading of different normal paraffins will reduce the capacity of adsorbents for the cyclic adsorption of chloride compounds. Light paraffins having three atoms or less as well as heavier paraffins having four carbon atoms or more cause a loss in adsorption capacity for chloride compounds when present in repeated adsorption and desorption cycles. The nature of the deactivation differs depending on the type of light hydrocarbons.

$C_3$ and lighter paraffins cause a decrease in desorption capacity that is roughly in proportion to their concentration. However, the loading capacity loss caused by the light hydrocarbons in the adsorption feed have been found to be only temporary.

The presence of heavier paraffins in a desorbent feedstream tend to cause a more gradual, but non-recoverable loss in chloride adsorption capacity after repeated adsorption and desorption cycles. The rate at which the adsorbent loses capacity for chlorides has been found to be proportional to the concentration of heavy normal paraffins present in the desorption stream. Decreases tend to occur linearly over the cycle life. For example, a desorption feed consisting of a fifty-fifty mixture of hydrogen and pentane linearly decreased the chloride adsorption capacity of a clinoptilolite adsorbent from 1.7 wt % to 0.3 wt % in 25 cycles when pentane portion was 100% normal pentane. A fifty-fifty mixture of pentane and hydrogen under the same adsorption and desorption conditions linearly decreased the adsorption capacity of the clinoptilolite adsorbent from 1.7 to 1.2 wt % in the same number of cycles when the pentane portion was 50% isopentane and 50% normal pentane. The loading losses from desorption of chloride compounds in the presence of normal butane and heavier normal paraffins has been found to be non-recoverable by hot hydrogen stripping and vacuum activation. Air calcination at temperatures of up to 370° F. were found to offer some improvement in the hydrogen chloride loading capacity of an adsorbent.

While not wishing to be bound by any theory, it is believed that the presence of the heavy normal paraffins creates surface pore clogging that makes the interior of the molecular sieve crystalline structure less accessible to the chloride compounds. Clogging of surface pores reduces the effective cyclic loading. Experiments have verified the pore clogging phenomenon by showing an increase in the mass transfer zone length after repeated cyclic loading using heavy normal paraffin desorbents.

Suitable desorbent streams for this invention will have a concentration of $C_4$ and heavier normal paraffins of less 10 wt %. More preferably the desorbent stream will have a concentration of $C_4$ and heavier normal paraffins of less than 1 wt % and more preferably of less than 0.1 wt %.

In a typical arrangement for the adsorption zone a fixed bed retains the adsorbent in the adsorption zone for contact with the input and effluent streams from the reaction zone. The adsorption zone preferably contains two or more adsorbent beds to continuously adsorb and desorb material from the effluent and the input stream. Typical conditions for operation of the adsorbent zones will again depend upon the particular adsorbents used and the temperature and pressure conditions of the inlet and effluent stream from the reaction zone. Typical conditions will include temperatures from 50°–750° F. and pressures of from 1 atmosphere to 50 atmospheres with the feedstream contacting the adsorbent in vapor or liquid phase conditions. Preferably, the processing conditions will maintain the feedstream through the adsorption zone in a vapor phase. The adsorption process will generally use temperature swing adsorption and desorption cycles with a typical temperature swing of from 100° F. to 330° F.

Operating conditions within the isomerization zone are selected to maximize the production of isoalkane product from the feed components and are influenced by the type of catalyst as well as the composition of the feed. Two reaction zones are typically provided due to a temperature rise that initially occurs from hydrogenation reactions. Conditions within the first isomerization zone typically include a temperature in the range of 190°–290° C. (375°–550° F.), a pressure of from 1200–3100 kPag (175–450 psig) and a liquid hourly space velocity of from 4–20. Typically, the reaction conditions are selected to keep the hydrocarbon feed in a vapor or mixed phase. Temperatures within the second conversion zone will usually operate at somewhat lower temperatures and range from about 65°–280° C.

(150°–536° F.). These lower temperatures are particularly useful in processing feeds composed of $C_5$ and $C_6$ paraffins where the lower temperatures favor equilibrium mixtures having the highest concentration of the most branched paraffins. When the feed mixture is primarily $C_5$ and $C_6$ paraffins, temperatures in the range of from 65°–160° C. (150°–320° F.) are preferred. When it is desired to isomerize significant amounts of $C_4$ hydrocarbons, higher reaction temperatures are required to maintain catalyst activity. Thus, when the feed mixture contains significant portions of $C_4$–$C_6$ paraffins most suitable operating temperatures are in the range from 140°–235° C. (280°–455° F.). The second conversion zone may be maintained over the same range of pressures given for the first conversion zone. The feed rate to the second conversion zone may also vary over a wide range but will usually include liquid hourly space velocities that are lower than the first conversion zone and range from 0.5–12 hr.$^{-1}$, with space velocities of between 1 and 8 hr.$^{-1}$ being preferred. The hydrogen concentration in the second conversion zone may also be adjusted by the addition of hydrogen to the feed or to the second conversion zone. The particular operating conditions within the isomerization zone will also be influenced by the makeup of the feed stream and the catalyst composition employed therein.

Side reactions within the isomerization zone, particularly the saturation of unsaturates, will raise the temperature of the effluent from the first conversion zone. For example, the effluent from the first conversion zone can increase by 20° F. for each percentage point of benzene that is present in the entering feed. As a remit of the increased temperature, the effluent from the first conversion zone is cooled in order to return it to a more desired isomerization temperature before it enters the second conversion zone. Even where there is not a substantial heat addition in the first conversion zone, it is often desirable to operate the second conversion zone in a two-stage isomerization process, at a lower temperature which, in the case of $C_5$–$C_6$ hydrocarbons will move the reaction equilibrium toward the production of isoparaffins. The cooling is particularly beneficial for the arrangement of this invention where exothermic reactions can raise the temperature of the reaction zone effluent above those that are most beneficial for adsorption.

Whether operating with one or more reactors the effluent from the isomerization zone will in most cases enter a separation zone for the removal of light gases from the isoparaffin containing product stream. The light gases include hydrogen added to the feed stream entering the first conversion zone and any additional hydrogen that was added to the feed entering the second conversion zone. At minimum, the separation facilities divide the conversion zone effluent into a product stream comprising $C_4$ and heavier hydrocarbons and a gas stream which is made up of lighter hydrocarbons and hydrogen. Suitable designs for rectification columns and separator vessels are well known to those skilled in the art. The separation section may also include facilities for recovery of normal alkanes. Normal alkanes recovered from the separation facilities may be recycled to either the first or second conversion zone to increase the conversion of normal alkanes to isoalkanes. $C_3$ and lighter hydrocarbons and any excess hydrogen from the second conversion zone are removed or returned to the process as part of the hydrogen gas stream.

The type of separation zone and the hydrogen concentration in the effluent will influence the placement of the adsorption zone for the recovery of chloride compounds. Traditional isomerization processes operated with a relatively high recycle of hydrogen. In order to conserve hydrogen and stabilize the effluent, the effluent from the isomerization zone will pass directly to a hydrogen separator when the hydrogen to hydrocarbon ratio exceeds about 0.05. Cooling ahead of the hydrogen separator will lower the remainder of the effluent stream to a temperature in a range of from 80°–140° F. Thus, the temperature condition of the effluent leaving the hydrogen separator is suitable for adsorption of chloride compounds. Where there is a hydrogen recycle, the chloride adsorber bed undergoing the adsorption step will normally receive the effluent stream passing from the hydrogen separator to a stabilizer for the separation of isomerate product from non-condensibles. Isomerization zone processes that operate with very low hydrogen concentrations in the feed and the effluent eliminate the hydrogen separator and an accompanying recycle compressor to reduce utility and capital cost. In these cases, the effluent stream passes directly from the isomerization reaction zone to the stabilizer. In most cases, the temperature of the effluent passing from the isomerization reaction zone to the stabilizer exceeds a suitable adsorption temperature. Therefore, where the isomerization reaction zone operates without hydrogen recycle, or in what is generally referred to as a hydrogen once-through operation, the effluent from the isomerization zone is cooled to place the chloride adsorber between the reactor and the stabilizer or the chloride adsorber generally adsorbs chloride compounds from the overhead of the stabilizer. Since most of the chloride compounds are contained in the stabilizer overhead, the isomerate from the stabilizer is still relatively free of chloride compounds and a majority of the chlorides are recovered for return to the isomerization reaction zone. Treating the overhead of the stabilizer has the advantage of virtually eliminating the presence of $C_4$ and higher hydrocarbons from the adsorbent bed even during the adsorption cycle.

Again, it is generally known that high chlorided platinum-alumina catalysts of this type are highly sensitive to sulfur and oxygen-containing compounds. A sulfur concentration of 0.5 ppm in the feed or less is required, since the presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water and oxygenate compounds are generally kept to a concentration of 0.1 ppm or less. The more stringent limitation on water and oxygenate compounds that decompose to form water stems from the fact that water can act to permanently deactivate the catalyst by removing high activity chloride from the catalyst and replacing it with inactive aluminum hydroxide.

Although sulfur compounds will not cause permanent deactivation, isomerization feeds will usually contain sulfur which will interfere with the isomerization operations. Sulfur contaminants are present with the original crude oil fraction and include mercaptans, sulfides, disulfides and thiophenes. For light straight run feeds, sulfur concentrations will usually range from 20–300 ppm. Rapid coking of the catalyst has been experienced in most cases following sulfur deactivation. If left unchecked, the coking will be severe enough to require a complete regeneration of the catalyst. Therefore, it is common practice to minimize the amount of sulfur that contacts catalyst in the isomerization zone to prevent deactivation and avoid a full regeneration of the catalyst.

A wide variety of adsorbents can be used for removing the sulfur from the feed. Suitable adsorbents for hydrogen sulfide include those adsorbents having a pore diameter of at least 3.6 Å, the kinetic diameter of hydrogen sulfide. Such adsorbents include Zeolite 5A, Zeolite 13X, activated carbon and other materials that are well known in the art and conventionally used for hydrogen sulfide adsorption. Particularly preferred adsorbents for the removal of hydrogen sulfide from the isomerization zone feedstream include 4A Zeolite and clinoptilolite molecular sieves. Zeolite 4A is the sodium form of Zeolite A and has pore diameters of about 4 Å. The method for its preparation and chemical and physical properties are described in detail in U.S. Pat. No. 2,882,243 the contents of which are hereby incorporated by reference.

Figure 1:
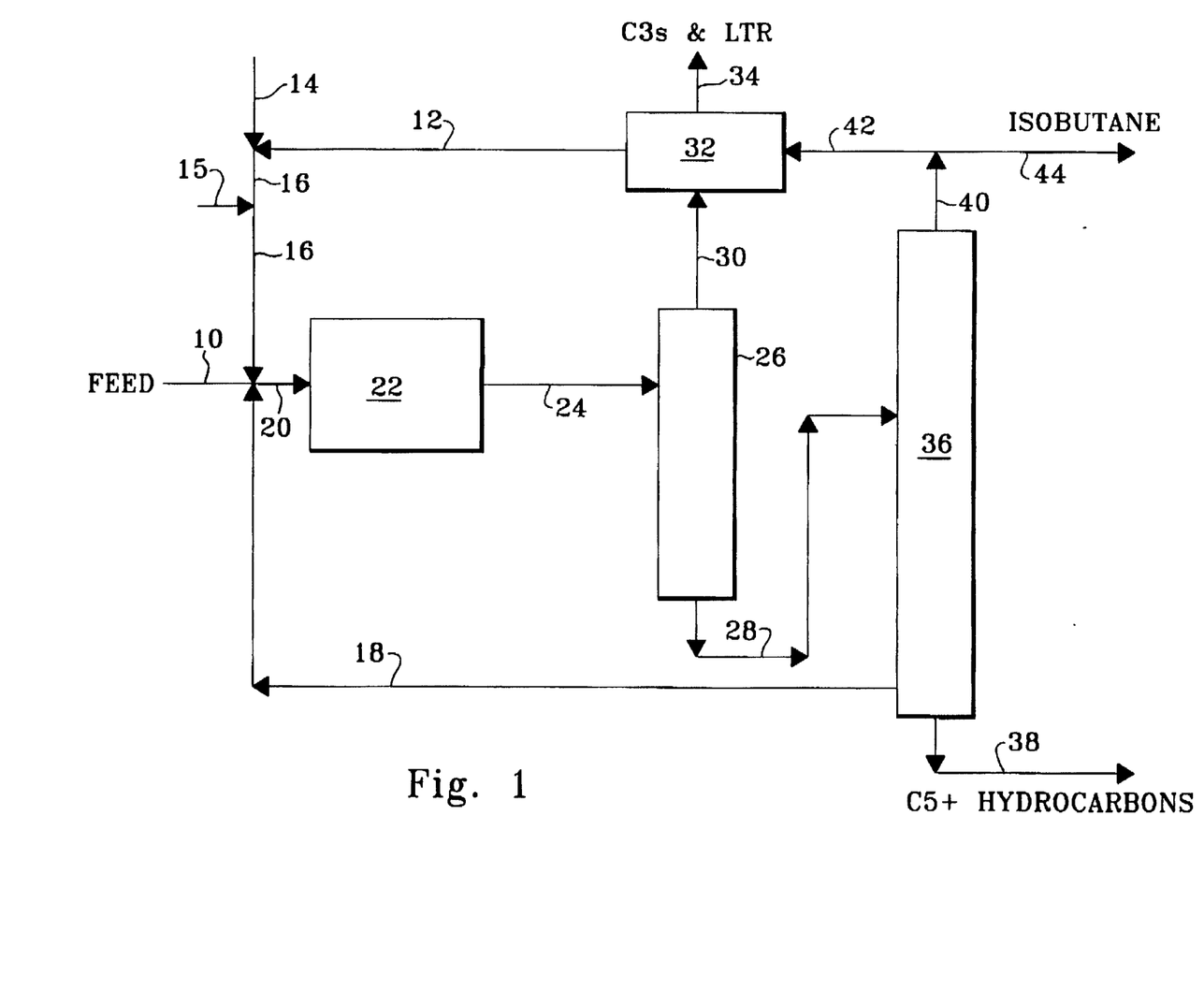
FIG. 1 is a process flow diagram for isomerizing a feed stream comprising normal hydrocarbons with a chloride promoted catalyst in accordance with this invention.

In order to demonstrate the preferred arrangement of this invention, an isomerization reaction zone using a chlorided platinum alumina catalyst and adsorptive chloride recovery section is depicted in FIG. 1. FIG. 1 is a schematic representation of the process and shows only the portions of the major equipment necessary to carry out the process. Other related equipment such as separators, pumps, compressors, coolers, condensers, reflux drums etc. which are well known to those skilled in the art have not been shown and are not necessary for an understanding of Applicant's invention or the underlying concepts.

In the isomerization process of FIG. 1, a hydrocarbon feedstream containing principally normal butane and lesser amounts of propane and pentanes enters the process through a line 10. A desorption stream 12 containing HCl and isobutane receives hydrogen from a hydrogen containing gas stream 14 to provide a stream 16 containing chloride and hydrogen that mixes with the feed. Hydrogen is added via line 14 in amounts that will produce a hydrogen to hydrocarbon ratio of less than 0.05. Preferably, the hydrogen-containing gas stream will have a hydrogen concentration greater than 75 wt. % hydrogen. A small amount of make-up chlorides are added to the line 16 via chloride input stream 15. A recycle stream 18 combines normal butane with the feed and stream 16 to provide a combined feed 20 that enters a butane isomerization zone 22. Reaction zone 22 schematically represents an isomerization zone that can consist of multiple reactors, feed exchangers and heaters The isomerization zone contains chlorided platinum alumina catalyst that contacts the feedstream and produces an isomerization zone effluent stream 24.

The effluent stream carried by line 24 enters a stabilizer zone 26 that separates lighter hydrocarbons and gases from heavier hydrocarbons in the entering effluent stream. A line 30 recovers $C_3$ and lighter hydrocarbons overhead after it passes through ordinary parts of a reflux system such as a condenser and an overhead drum which are contained within the stabilizer zone 26. Stabilizer 26 separates a bottoms stream 28 containing $C_4$ and heavier hydrocarbons and minor amounts of $C_3$ hydrocarbons from the isomerization zone effluent. Line 30 recovers the remainder of the isomerization zone effluent as a net overhead stream from the stabilizer that contains less than 2 wt % $C_4$ and higher normal paraffins.

The net overhead stream 30 passes through a series of adsorption vessels within an adsorption zone 32 that contains as the adsorbent a clinoptilolite molecular sieve selected for the removal of chloride compounds from the overhead stream and resistance to the corrosive effects of the chloride compounds. Passage through the series of adsorbers within adsorption zone 32 produces an essentially chloride-free net overhead stream that contains $C_3$ and lighter material. Adsorption vessels within adsorption zone 30 operate in cyclic fashion. A line 34 recovers a substantially chloride-free stream from adsorption zone 32. Stream 34 may be further processed for the recovery of hydrocarbons and gaseous components or, is more typically used as a fuel gas stream.

Hydrocarbon liquid comprising the main product stream from the isomerization zone exits the stabilizer zone through line 28. Line 28 will typically receive liquid from a reboiler arrangement that is contained within the stabilizer zone 26. The stabilizer bottoms stream passes to a deisobutanizer column 36 that produces an isobutane rich stream 40, a bottoms stream of $C_5$ and heavier hydrocarbons and normal butane recycle stream 18.

A line 42 withdraws a small portion of an isobutane rich gas stream from the net deisobutanizer overhead 40 for desorbing chloride containing adsorbent in the adsorption zone 32. The isobutane stream contacts chloride containing adsorbent in an adsorber vessel that was formerly in an adsorption mode. The amount of isobutane needed from the net isobutane overhead stream for desorbing chloride compounds from the adsorber beds of adsorption zone 32 is less than 10% of the net overhead from the deisobutanizer and, more typically less than 2% of the net overhead. The chloride containing desorption fluid exits adsorption zone 32 via line 12 and supplies the majority of the chloride needed for the promotion of the isomerization catalyst in reactor zone 22. Any small chloride losses are replaced by the additional chloride compounds from line 15.

EXAMPLES

The following examples were run to determine what effect the presence of normal paraffins had on the continued adsorption activity of clinoptilolite adsorbents. A series of tests were run in a pilot plant containing interchangeable adsorbers for the testing of one adsorbent loaded adsorber at a time. The adsorber supported a bed approximately ⅝ inch in diameter by approximately 9¾ inches long. Chromatographic columns were arranged to measure HCl content in the adsorption and desorption effluent from the adsorbers. The tests used experimental conditions of 100° F. and 214 psia for adsorption and 330° F. and 214 psia for desorption. In each experiment NaK clinoptilolite was contained in each bed.

Example I

Figure 2:
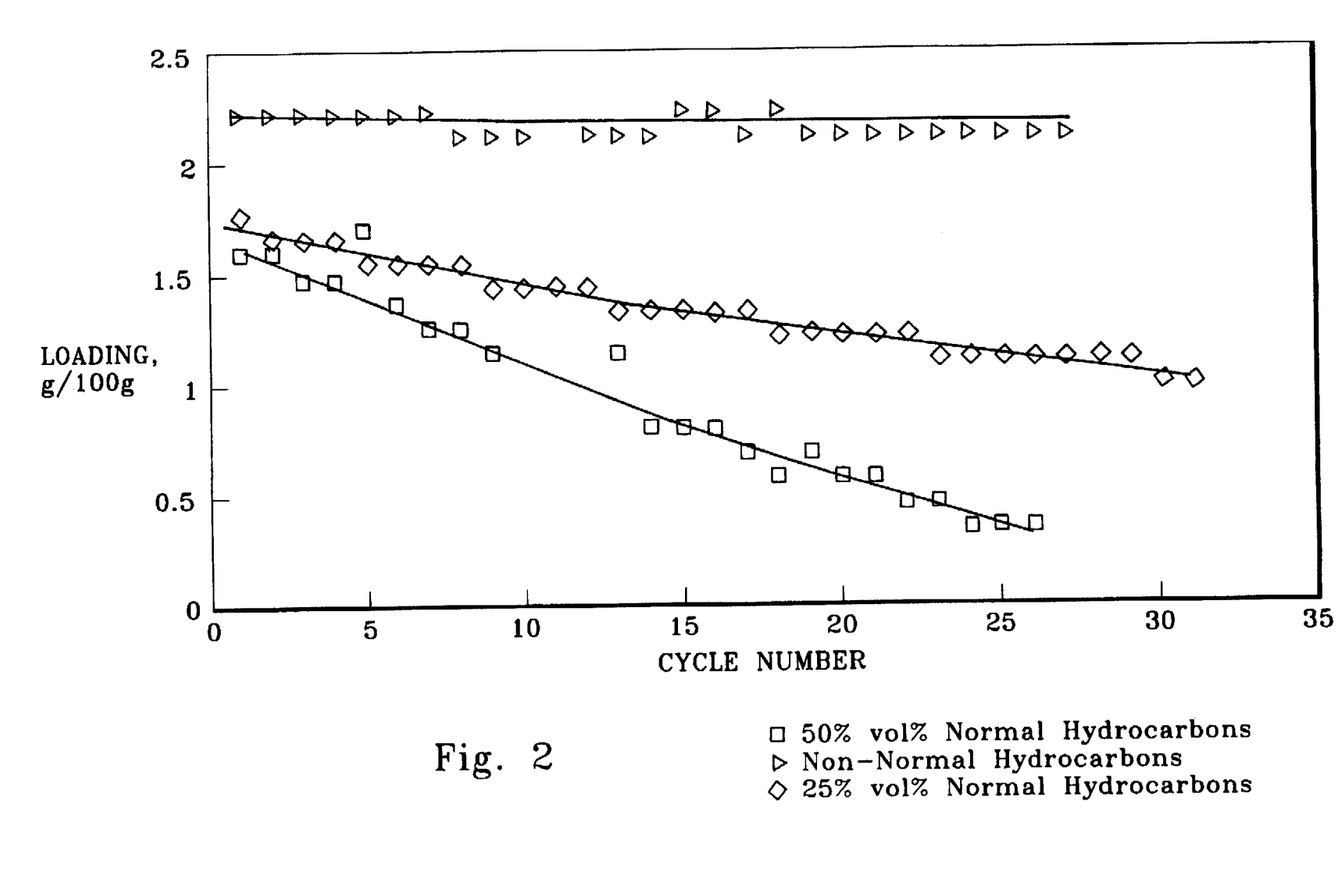
FIG. 2 is a graph showing the effect of normal pentane on the adsorption capacity of an acid resistant adsorbent.

An adsorber containing a 28.5 gram sample of NaK clinoptilolite adsorbent which had been subjected to two passes of calcination at a temperature of 600° F. was cyclically contacted with a feed and a desorbent. The feed consisted of hydrogen containing 1798 PPMV hydrogen chloride. The feed flow rate through the adsorption step was approximately 800 cm³/min. Time until breakthrough was recorded for each adsorption cycle and the total weight percent loading at breakthrough for each cycle was recorded. Desorption was carried out for one hour in each cycle using a fifty-fifty mixture of normal pentane and isopentane at a flow rate of 1 cm³/min pentanes. Methane and ethane were excluded from these samples to avoid co-adsorption in order more readily to distinguish trends in the adsorption capacity of the adsorbent. As shown in FIG. 2, the loading steadily declined from an initial loading of 1.6 wt % HCl to 0.46 wt % in 28 cycles. These test results established that the adsorbent was not commercially practical since the presence of methane and ethane—if added—would cause a further decrease in the adsorption capacity of the adsorbent.

Example II

Another experiment was conducted to confirm that normal pentane was causing the deactivation. This experiment used the identical feed conditions and adsorption procedure as Example I. This experiment differed from the previous pentane desorption experiment and used a fifty-fifty mixture on molar basis of pentane and hydrogen as a regenerant. The pentane again comprised a fifty-fifty mixture of isopentane and normal pentane resulting in a total normal pentane concentration of 25% on a volume basis. As FIG. 2 demonstrates, the adsorbent immediately began deactivating upon addition of the pentane with a decrease in capacity from 1.77 wt % to about 1 wt % within 30 cycles. It is believed that the partial pressure of the hydrogen suppressed coke formation or the amount of pore clogging thereby decreasing the rate of the deactivation. However, there is no indication that the deactivation was leveling off. Therefore, although the addition of the hydrogen decreased the deactivation rate by about a factor of 2, it is not sufficient to arrest deactivation.

Example III

Another experiment was performed using a normal pentane free isopentane as a regenerant. Adsorption and desorption were again carried out in cycle steps of 4 hours and 1 hour, respectively. The feed during the adsorption step consisted of a hydrogen stream with 2200 PPMV HCl at a total flow rate of 772 cc/min. The adsorber apparatus retained approximately 34 grams of a NaK clinoptilolite prepared in substantially the same manner as that used in Example I. The desorbent for the first 27 cycles was a pure isopentane that passed through the adsorption zone at a flow rate of 1 cc/min. As shown in FIG. 2, over the course of 27 cycles, the adsorbent provided a stable loading capacity of not less than 2.1 wt % HCl.

Example IV

Figure 3:
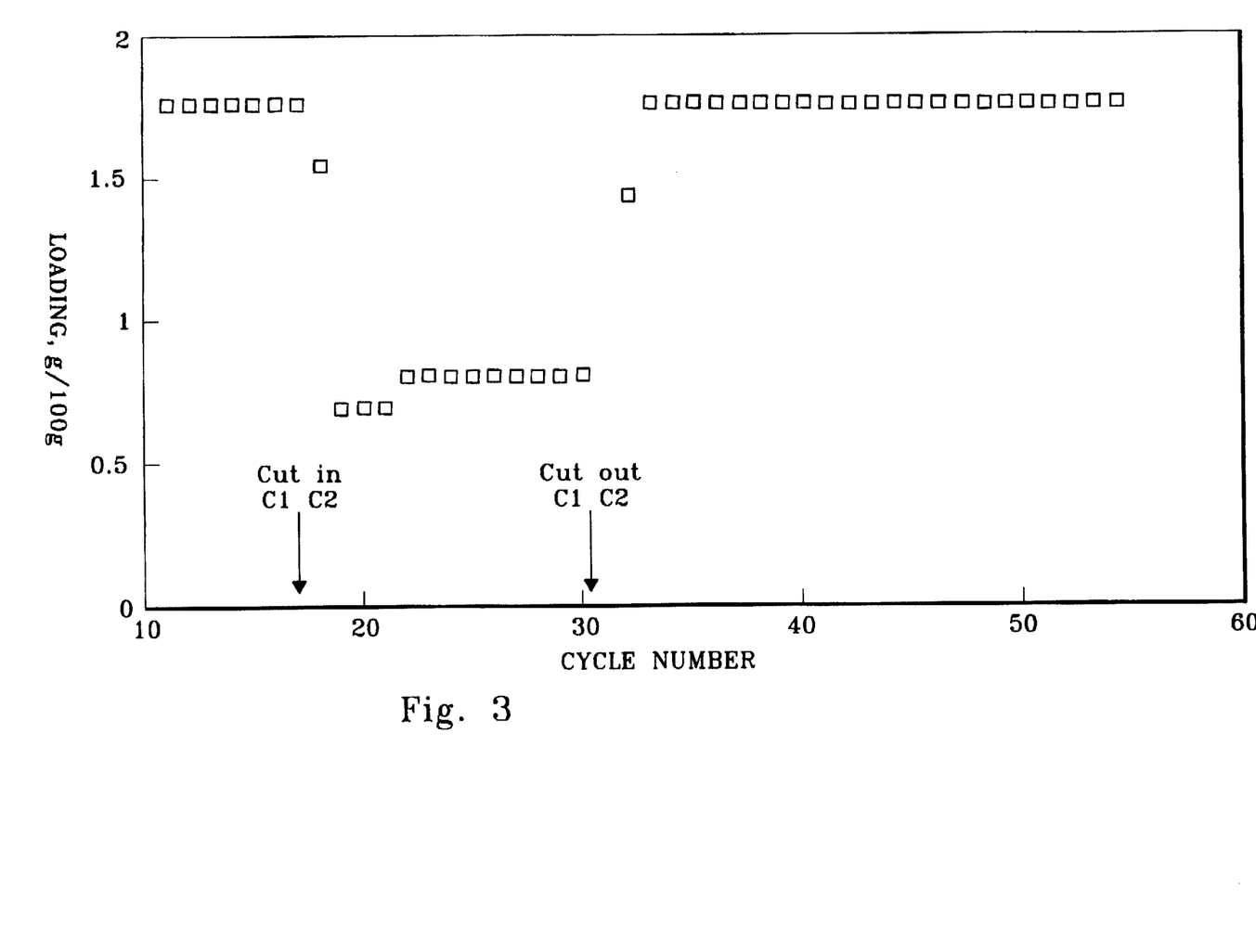
FIG. 3 is graph showing the effect of methane and ethane on the adsorption capacity of an acid resistant adsorbent.

The adsorption capacity loss and recovery due the presence of methane and ethane in the adsorption feed was investigated by charging 795 cc/min of a feedstream containing 250 cc/min of $C_1$–$C_2$ and 1823 PPMV of HCl to an adsorber containing 29.38 grams of a sodium and potassium exchange clinoptilolite adsorbent. The adsorption and desorption cycles were essentially the same as those previously described except that the desorbent consisted of hydrogen at a flow rate of 250 scc/min. The initial flow rate to the adsorption zone consisted of 45 cc/min of HCl and 761 cc/min of hydrogen. At about 18 cycles, about 250 cc/min of the hydrogen flow was replaced with a $C_1$–$C_2$ mixture. After about 30 cycles, the $C_1$–$C_2$ flow with the feed to the adsorption stream was again replaced with hydrogen. FIG. 3 dramatically illustrates the immediate effect of the methane and ethane to cause a sudden drop in HCl capacity. Just as dramatically, FIG. 3 illustrates how the removal of the $C_1$–$C_2$ from the feed caused an immediate return to the original capacity of the adsorbent. This testing illustrates that light paraffins have the immediate effect of dramatically reducing adsorption capacity for HCl of the adsorbents. This reduced capacity is immediately recovered upon removal of the methane or ethane.

These examples demonstrate that the elimination of heavy normal paraffins from the desorbent stream of a chloride adsorption zone will prevent progressive deactivation of the adsorbent and the loss of the adsorbent's capacity for adsorption of chloride compounds. The data also demonstrates that light paraffins create temporary deactivation of adsorption capacity of the adsorbents for chloride compounds.

We claim:

1. A process for the isomerization of a hydrocarbon feed containing normal paraffins with a chloride promoted catalyst, said process comprising:
   (a) combining a feed stream comprising normal paraffins with a first desorption stream comprising a chloride compound and containing less than 10 wt % normal paraffins to produce a combined feedstream;
   (b) contacting said combined feedstream with a chloride promoted isomerization catalyst at isomerization conditions to convert normal paraffins to isoparaffins and produce an effluent stream comprising normal paraffins, isoparaffins and a chloride compound;
   (c) passing at least a portion of said effluent to an adsorption zone and contacting the portion of said effluent with an adsorbent to adsorb chloride compounds from said effluent stream;
   (d) passing a second desorbent stream containing less than 10 wt % normal paraffins to said adsorption zone to desorb chloride compounds from said adsorbent and produce said first desorption stream; and,
   (e) recovering isoparaffins from said effluent stream.

2. The process of claim 1 wherein said feed comprises normal paraffins having from 4 to 6 carbon atoms.

3. The process of claim 1 wherein said desorption stream comprises isoparaffins.

4. The process of claim 1 wherein said effluent stream passes from said isomerization zone to a separator that produces an overhead stream comprising $C_3$ and lighter gases that contains chloride compounds and said overhead stream provides said portion of said effluent stream that passes to said adsorption zone.

5. The process of claim 1 wherein said adsorbent comprises a clinoptilolite molecular sieve.

6. The process of claim 1 wherein an isoparaffin stream is separated from said effluent stream and a portion of said isoparaffin stream passes to said adsorption zone as said desorbent stream.

7. The process of claim 1 wherein said feedstream comprises normal pentane and hexane.

8. The process of claim 7 wherein said desorbent stream comprises isopentane.

9. The process of claim 1 wherein said feedstream comprise normal butane and said desorbent stream comprises isobutane.

10. The process of claim 1 wherein said adsorption zone recovers at least 90 wt. % of said chloride compound from said effluent stream.

11. The process of claim 4 wherein said adsorption zone recovers at least 99 wt. % of said chloride compound from said overhead stream.

12. The process of claim 1 wherein said chloride compound comprises HCl.

13. A process for the isomerization of a hydrocarbon feed containing normal paraffins with a chloride promoted catalyst, said process comprising:
   (a) combining a feed stream comprising normal paraffins with a desorption stream comprising isoparaffins and a desorbed chloride compound to produce a combined feedstream;
   (b) contacting said combined feedstream with an chloride promoted isomerization catalyst at isomerization conditions to convert normal paraffins to isoparaffins and produce an effluent stream comprising normal paraffins, isoparaffins and a chloride compound;
   (c) passing said effluent stream to a first separator and recovering an overhead stream containing said chloride compound and a bottoms stream comprising normal paraffins and isoparaffins;

(d) passing said overhead stream to an adsorption zone and contacting said overhead stream with an clinoptilolite molecular sieve to adsorb said chloride compound from said overhead stream;

(e) passing said bottoms stream to a second separator to separate normal paraffins from isoparaffins and recovering an isoparaffin stream rich in isoparaffins;

(f) passing a portion of said isoparaffin stream to said adsorption zone to desorb chloride compounds from said adsorbent and produce said desorption stream comprising isoparaffins and chloride compounds; and, (g) recovering a portion of said isoparaffin stream from the process.

14. The process of claim 13 wherein first separation zone separates said effluent stream into a gaseous phase overhead stream and a liquid phase bottoms stream.

15. The process of claim 13 wherein the adsorbent having capacity for a chloride compound is selected from the group consisting of Na and K, Mg and K and barium ion-exchanged clinoptilolite.

16. The process of claim 13 wherein said feedstream comprises hydrocarbons having from 4 to 6 carbon atoms.

17. The process of claim 13 wherein said overhead stream comprises $C_3$ hydrocarbons and lower boiling material.

18. The process of claim 13 wherein said second separator recovers recycle stream comprising normal paraffins and said normal paraffins are recycled to said isomerization zone.

19. The process of claim 13 wherein said chloride compound comprises HCl.

20. A process for the isomerization of a normal butane with a chloride promoted catalyst, said process comprising:

(a) combining a feed stream comprising normal butane with a desorption stream comprising isobutane, a desorbed chloride compound and a normal butane recycle stream to produce a combined feedstream;

(b) contacting said combined feedstream with an chloride promoted isomerization catalyst at isomerization conditions to convert normal butane to isobutane and produce an effluent stream comprising normal butane, isobutane, a chloride compound and $C_3$ and lower boiling materials;

(c) passing said effluent stream to a stabilizer and recovering a gaseous overhead stream comprising $C_3$ and lower boiling materials and said chloride compound and a liquid bottoms stream comprising normal butane and isobutane;

(d) passing said gaseous overhead stream to an adsorption zone and contacting said overhead stream with an clinoptilolite molecular sieve to adsorb said chloride compound from said overhead stream;

(e) passing said bottoms stream to a deisobutanizer to separate normal butane from isobutane and recovering an isobutane overhead stream;

(f) passing a portion of said isobutane overhead stream to said adsorption zone to desorb chloride compounds from said adsorbent and produce said desorption stream comprising isobutane and chloride compounds;

(g) recovering a portion of said isoparaffin stream from the process; and, (h) recovering said normal butane recycle stream from said deisobutanizer column.

* * * * *